United States Patent [19]

Antoshkiw et al.

[11] 4,105,022
[45] Aug. 8, 1978

[54] METHOD OF DETERMINING CARDIAC OUTPUT BY THERMODILUTION PRINCIPLES AND UTILIZATION OF A CATHETER ASSEMBLY

[75] Inventors: William T. Antoshkiw, Clifton; Thomas A. Ursic, Hasbrouck Hts., both of N.J.

[73] Assignee: Becton, Dickinson and Company, East Rutherford, N.J.

[21] Appl. No.: 743,464

[22] Filed: Nov. 19, 1976

Related U.S. Application Data

[62] Division of Ser. No. 689,487, May 24, 1976, Pat. No. 4,024,873.

[51] Int. Cl.$^2$ .................................................. A61B 5/02
[52] U.S. Cl. .................................. 128/2.05 F; 73/204; 128/2.05 V; 128/349 B
[58] Field of Search ............... 128/2.05 F, 2.05 V, 128/2.05 R, 349 B, 349 BV; 73/204

[56] References Cited

U.S. PATENT DOCUMENTS

| 281,043 | 7/1883 | Finney | 128/349 BV |
|---|---|---|---|
| 2,912,981 | 11/1959 | Keough | 128/349 B |
| 3,359,974 | 12/1967 | Khalil | 128/2.05 F |
| 3,561,266 | 2/1971 | Auphan et al. | 128/2.05 F |
| 3,620,207 | 11/1971 | Sinclair | 128/2.05 F |
| 3,838,683 | 10/1974 | Kolin | 128/2.05 F |
| 3,995,623 | 12/1976 | Blake et al. | 128/2.06 E |

FOREIGN PATENT DOCUMENTS

2,302,156   7/1974   Fed. Rep. of Germany ...... 128/2.05 F

OTHER PUBLICATIONS

Ellis, R. J. et al., *Journ. of Assoc. for Advance of Med. Instr.* vol. 6, No. 2, Mar.-Apr., 1972, pp. 116-121.

*Primary Examiner*—Kyle L. Howell
*Attorney, Agent, or Firm*—Kane, Dalsimer, Kane, Sullivan & Kurucz

[57] ABSTRACT

A method for determining cardiac output by use of thermodilution principles and by utilizing a catheter assembly with a passageway therethrough. The catheter assembly is introduced at least into close proximity to the right heart. A small balloon tipped catheter is inserted through the passageway of the catheter assembly and is guided thereby with the balloon uninflated and with a thermistor attached thereto to the desired location. The balloon tipped end of the small catheter is passed out of the passageway through the catheter assembly into the bloodstream and the balloon is inflated so that it is flow directed away from the catheter assembly into the desired position in the heart and spaced a substantial distance from the catheter assembly. The small balloon tip catheter has a central lumen therethrough to effect the inflation and deflation of the balloon. A fluid different in temperature from the bloodstream is injected into the annular space between the passageway of the catheter assembly and the other surface of the smaller balloon tipped catheter with the passageway through the catheter assembly forming a guideway for the fluid to direct it to the desired location and the spacing between the inflated small balloon catheter and the catheter assembly preventing interference of the flow of the fluid from the catheter assembly so that the thermistor on the balloon catheter can detect the temperature changes in the bloodstream. The thermistor output is then detected to determine the cardiac output.

5 Claims, 3 Drawing Figures

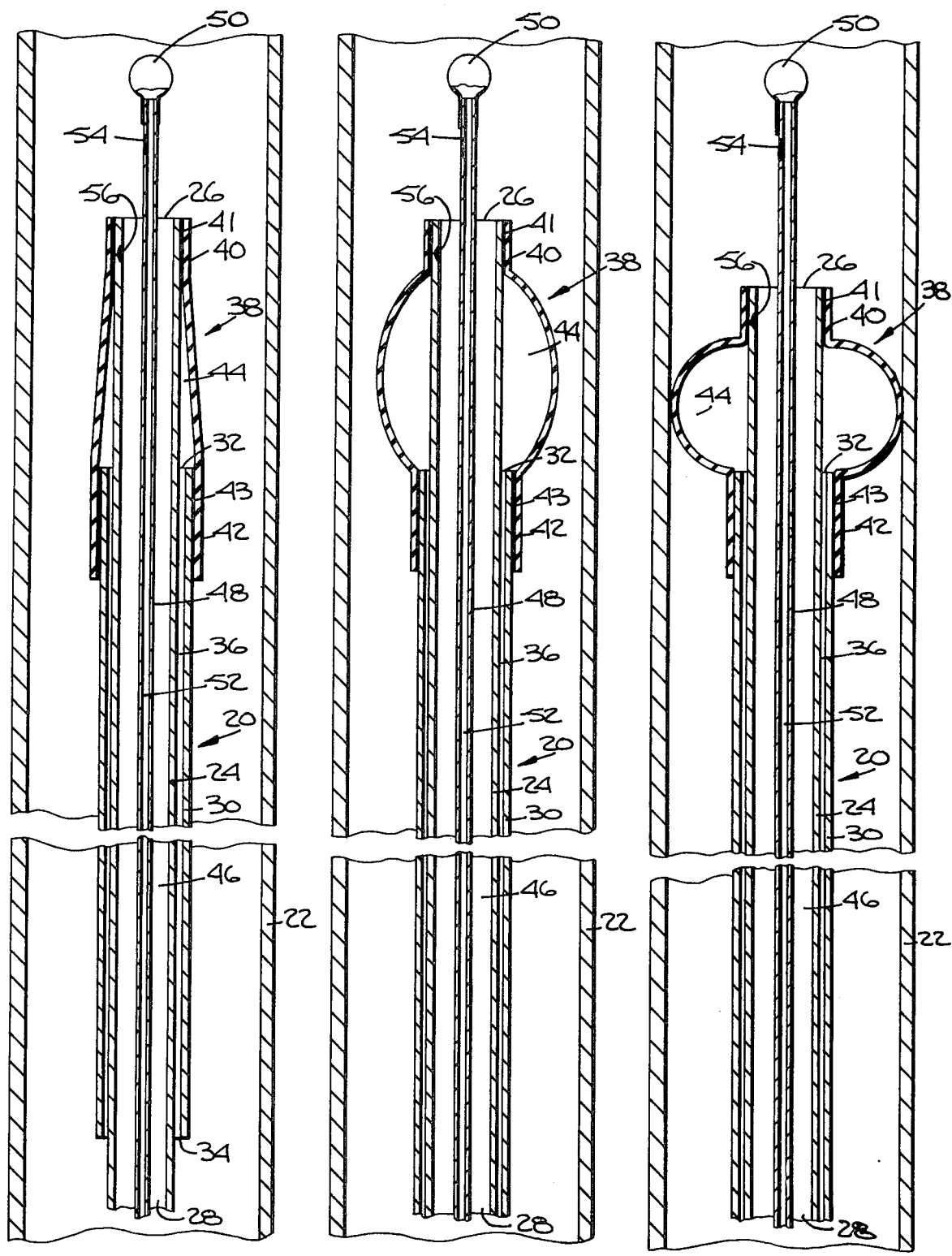

METHOD OF DETERMINING CARDIAC OUTPUT BY THERMODILUTION PRINCIPLES AND UTILIZATION OF A CATHETER ASSEMBLY

CROSS REFERENCE TO RELATED APPLICATION

This application is a divisional application of prior application Ser. No. 689,487 filed on May 24, 1976, now U.S. Pat. No. 4,024,873.

BACKGROUND OF THE INVENTION

There has long been a need for a multi-component flow directed catheter system for use in the determination of physiological parameters in the vascular system as well as for other diagnostic purposes in connection with the human vascular system. For example, in present thermodilution procedures utilized in determining cardiac output, the results are often altered by physiological parameters which the procedures are attempting to measure. Naturally it is desirable to minimize these negative effects.

SUMMARY OF THE INVENTION

The ballon catheter system of the present invention is directed to a multi-component flow directed catheter system for use in the determination of physiological parameters in the vascular system. The central component of the system is a ballon tipped catheter which, by means of flow directed ballon tip, forms or acts as a passageway from outside of the body to the interior of the heart, in particular, the right heart including the right atrium, the right ventricle and the pulmonary artery. The catheter system includes an arrangement which provides the capability of altering the shape of the balloon portion of the system while in vitro and/or in vivo.

The basic catheter assembly consists of two or more concentric tubes with the inside tube extending at least distally beyond the outside tube. A balloon is attached distally to the inside tube. The distal attachment of the balloon to the inside tube in effect seals the distal portion of the balloon. Proximally the balloon is attached to the outside catheter and in effect seals the proximal portion of the ballon. The ballon, therefore, is attached distally to the inside tube and proximally to the outside tube. Inflation and deflation is effected by injecting or withdrawing gas, such as air or carbon dioxide, or liquid into the annular space between the two tubes which is sealed distally by an appropriate adapter or connector apparatus. The apparatus not only provides the means of sealing the annular space distally, but also provides a passageway to inject or withdraw air or gas into the annular space, typically by means of a syringe or similar device. The catheter assembly also provides the capability of moving the inside tube axially with respect to the outside tube. This movement affects the distance between the distal and proximal attachments of the balloon and thereby affects the shape of the balloon while in vitro or in vivo.

As required, various transducers for pressure, temperature, and the like, can be attached to the distal portion of the catheter assembly, distal to, proximal to or within the balloon structure itself. Wires to the transducers can be placed either in the annular space between the inner and outer tubes or within the side walls of the outer and/or inside tubes.

The principle of the catheter assembly described above is part of a total approach to determine physiological parameters specifically as part of diagnostic procedures involving the right heart. The lumen of the inner tube forms a passageway from outside the body to the atrium and/or ventricle. Through this lumen, it is intended that a complete system of specialized probe-like instruments can be passed such as a pressure transducer tipped probe for determining pressure, a fiberoptic probe for determining carbon dioxide or oxygen concentrations, or a probe for a thermodilution system for determining cardiac outputs. The lumen through the inner tube also acts as a passageway for the withdrawal or injection of fluids into or out of the body.

It is also contemplated among the objectives of the present invention to utilize the balloon catheter system of the present invention in other areas of the body. For example, it can be used in connection with biopsy type instruments passed through the lumen to obtain specimens. For biospy procedures, the balloon not only serves for flow direction but also to firmly wedge the catheter in the vessel to prevent recoil during the obtaining of the biopsy.

As stated above, the present balloon catheter system is particularly adapted for use as part of a system for determining cardiac output by means of thermodilution principles. In the process, the catheter assembly described above is introduced into or in close proximity to the right heart. Then, through the lumen of the inner tube, a small balloon tipped catheter is inserted with the balloon uninflated. Once the catheter is passed out of the lumen of the inner tube into the blood stream, the balloon is inflated and is flow directed away from the remainder of the catheter assembly into the heart. A thermistor is attached to the small balloon catheter proximally to the balloon. The tubing of the small balloon catheter has a central lumen to effect the inflation and deflation of the balloon. The balloon is sealingly engaged with the distal end of the tubing and acts as the distal tip for the inner catheter. The wires to the thermistor are placed either in the lumen or in the side walls of the catheter.

A fluid, different in temperature from the blood stream, is then injected in the annular space between the lumen of the inside tube of the main catheter assembly and the balloon tipped probe. The thermistor on the balloon probe detects the temperature changes in the bloodstream. An additional thermistor can be attached to the distal portion of the main catheter assembly to facilitate accurate measurement of the temperature of the injectate at the exact moment it mixes with the bloodstream.

The small balloon catheter provides an advantageous feature in that it will not disrupt the flow of blood as much as a larger catheter would. Also, the relative positions of the thermistors can be altered according to where the body blood flow rate determinations are being made. Furthermore, flow rate determinations may be made with the main catheter assembly balloon in either the inflated or deflated state. The main catheter assembly can also be used by itself for such procedures as aterial dilations. In summary, the present invention deals with a unique balloon catheter design and a unique method for determining blood flow via thermodilution as well as other objectives including those discussed above.

With the above objectives in mind, reference is made to the attached drawings.

BRIEF DESCRIPTION OF THE DRAWINGS

In the Drawings:

FIG. 1 is a fragmentary sectional view of the balloon catheter assembly of the present invention shown in position within a patient and with a small balloon tipped catheter inserted therethrough for diagnostic use therewith;

FIG. 2 is a fragmentary sectional view thereof showing the same components in position with the balloon portion of the main catheter in inflated condition;

FIG. 3 is a sectional view thereof with the inflated balloon portion of the main catheter assembly having been altered in shape by relative movement between the inner and outer tubes.

DESCRIPTION OF THE PREFERRED EMBODIMENTS

FIGS. 1–3 of the drawings show the balloon catheter assembly of the present invention as used in cooperation with a small balloon tipped catheter in a thermodilution procedure. The main catheter assembly 20 is inserted within the appropriate vessel 22 of the patient in a conventional manner. As shown in FIG. 1, the catheter assembly 20 includes an inner tube 24 having an open distal end 26 and an open proximal end 28. Surrounding tube 24 in concentric relationship is an outer tube 30 terminating in an open distal end 32 and an open proximal end 34 which are positioned so that the inner tube 24 extends distally and proximally from the ends of the outer tube 30.

The outer diameter of inner tube 24 is less than the inner diameter of outer tube 30 so that the inner tube extends freely through the lumen of the outer tube and provides an annular space 36 therebetween.

An inflatable balloon portion 38 is attached to both the inner and outer tubes. The distal end 40 of the balloon portion is affixed to the outer surface of the distal end of the inner tube and the proximal end 42 of the inflatable portion 38 is attached to the outer surface of the distal end of the outer tube 30. The interengagement therebetween can be of a conventional nature such as by epoxy. All of the components of the assembly can be of a conventional plastic and in addition the inflatable balloon can be of a more flexible material if desired such as natural or synthetic rubber. By sealing both ends of the balloon portion 38 to the tubes 24 and 30, an inner chamber 44 is formed in the balloon portion with the only access to inner chamber 44 being through the annular passageway 36 between the tubes.

Accordingly, if it is desired to inflate the balloon portion 38, a suitable inflation medium such as a gas like air or carbon dioxide or a liquid can be passed in a conventional manner through the opening 34 at the proximal end of outer tube 30, through annular passageway 36 and into chamber 44 to thereby expand the flexible balloon 38 into a configuration such as depicted in FIG. 2.

Thereafter, the inflated balloon 38 can be altered in configuration, as desired, by merely shifting the relative axial position between inner tube 24 and outer tube 30 as depicted in FIG. 3 where the inner tube has been withdrawn rearwardly toward the outer tube thereby causing the affixed balloon to deform outwardly into engagement with the walls of the vessel 22. In this manner, it is possible to manipulate assembly 20 so as to utilize the tubes and innterconnected balloon portion to obtain the desired configuration within the vessel.

As previously discussed, the lumen 46 through the inner tube 24 is open at both ends so that appropriate instruments can be passed therethrough for procedures being carried out. In the depicted form, the catheter assembly 20 is shown in use as part of a thermodilution procedure for determining cardiac output.

The main catheter assembly 20 is positioned in the vessel 22 into or in close proximity to the right heart. Then, through the lumen 46 of inner tube 24, a small catheter 48 is passed having its forward tip covered and sealed by a small balloon 50. The lumen 52 of the small catheter 48 communicated with the interior of sealed small balloon 50 at the distal tip and extends rearwardly where it can be connected in a conventional fashion to a source of pressure to inflate the balloon 50. The catheter 48 is inserted through lumen 46 with the balloon 50 uninflated. Once the catheter passes through distal open end 26 and into the blood-stream, the balloon 50 can be inflated through lumen 52 in catheter 48 and it is then flow directed away from catheter assembly 20 into the heart.

A thermistor 54 is attached to the catheter 48 proximal to balloon 50. The wires to thermistor 54 can be placed either in the lumen 52 or in the side walls of catheter 48.

A fluid, different in temperature from the bloodstream, is then injected in the lumen 46 of inner tube 24 between the walls forming the lumen and the outer surface of catheter 48. The thermistor 54 on the balloon probe of catheter 48 detects the temperature changes in the bloodstream. A second thermistor 56 can be attached to the distal portion of the inner tube 24 to accurately measure the temperature of the injectate at the exact moment it mixes with the bloodstream in the vessel 22.

The small catheter 48 does not disrupt the flow of blood as much as could happen with a larger catheter. Also, the relative positions of thermistor 54 and 56 can be altered according to where the body blood flow rate determinations are being made. As discussed, the wires for the thermistor can be placed either in the lumens or in the side walls of the catheters on which the thermistors are mounted. Flow rate determinations may be made with the same main catheter balloon 38 in either the inflated or deflated state. Furthermore, catheter assembly 20 itself can also be used for such procedures as aterial dilations. It is also contemplated that a catheter assembly of more than two concentric tubes can be provided, or a transducer attached to the distal portion of the assembly, for a desired medical procedure.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. A method for determining cardiac output by means of thermodilution principles and by utilizing a catheter assembly with a passageway therethrough comprising; introducing the catheter assembly at least into close proximity to the right heart, inserting a small balloon tipped catheter with the balloon uninflated through the passageway of the catheter assembly and with a thermistor attached thereto with the passageway of the catheter assembly forming a guideway for directing the small balloon catheter to the desired location, passing the balloon tipped portion of the small catheter out of the passageway of the catheter assembly into the bloodstream and inflating the balloon so that the balloon is flow directed away from the catheter assembly into the heart and spaced from the catheter assembly a substantial distance to facilitate prevention of interference between the passageway through the catheter assembly and the inflated tip portion of the small catheter, providing a central lumen in the small balloon tipped catheter to effect the inflation and deflation of the balloon, injecting a fluid different in temperature from the blood stream into the annular space between the passageway of the catheter assembly and the outer surface of the inflated balloon tipped portion of the small catheter spaced therefrom whereby the thermistor of the balloon catheter detects the temperature changes in the bloodstream, and detecting the thermistor output to determine cardiac output.

2. The invention in accordance with claim 1 wherein the smaller balloon tipped catheter is formed by attaching the thermistor at a location proximal to the balloon tip so that when the inflated balloon tip is flow directed away from the catheter assembly the thermistor will be spaced from the catheter assembly.

3. The invention in accordance with claim 1 wherein inflation of the balloon on the small catheter is produced only by passing fluid through the lumen of the small catheter and directly into the balloon sealingly mounted on the tip thereof.

4. The invention in accordance with claim 1 wherein the step of attaching a second thermistor to the distal portion of the catheter assembly is provided to accurately measure the temperature of the injectate at the moment it mixes with the bloodstream.

5. The invention in accordance with claim 1 wherein the catheter assembly is formed by concentrically arranging two tubes with distal and proximal ends and with the inner tube being spaced from the inner wall of the outer tube, extending the distal end of one of the tubes beyond the distal end of the other tube and the tubes being axially displaceable with respect to one another, mounting an inflatable catheter assembly balloon on the tubes with one end thereof mounted on the distal end portion of one of the tubes and its other end mounted on the distal end portion of the other of the tubes so as to seal the catheter assembly balloon from the exterior of the tubes, providing openings at both ends of one of the tubes to permit access therethrough from end to end and the passageway through the catheter assembly for insertion of the small balloon tipped catheter therethrough, and the other tube having its distal end in communication with the interior of the catheter assembly balloon and its proximal end adapted to be connected to a source of fluid for expanding the catheter assembly balloon.

* * * * *